US 6,750,221 B1

(12) United States Patent
Garcia-Ladona et al.

(10) Patent No.: US 6,750,221 B1
(45) Date of Patent: Jun. 15, 2004

(54) USE OF 5-HT5-LIGANDS IN THE TREATMENT OF NEURODEGENERATIVE AND NEUROPSYCHIATRIC DISTURBANCES

(75) Inventors: Francisco Javier Garcia-Ladona, Kandel (DE); Laszlo Szabo, Dossenheim (DE); Gerd Steiner, Kirchheim (DE); Hans-Peter Hofmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/889,157

(22) PCT Filed: Jan. 11, 2000

(86) PCT No.: PCT/EP00/00143

§ 371 (c)(1),
(2), (4) Date: Jul. 11, 2001

(87) PCT Pub. No.: WO00/41696

PCT Pub. Date: Jul. 20, 2000

(30) Foreign Application Priority Data

Jan. 11, 1999 (DE) .......................................... 199 00 673

(51) Int. Cl.$^7$ ............................................. A61K 31/505
(52) U.S. Cl. ....................................................... 514/267
(58) Field of Search ......................................... 514/267

(56) References Cited

U.S. PATENT DOCUMENTS

| 5,807,691 A | 9/1998 | Amlaiky et al. ................ 435/7 |
| 6,387,912 B1 | 5/2002 | Steiner et al. .............. 514/258 |

FOREIGN PATENT DOCUMENTS

| DE | 196 36 769 | 3/1998 |
| DE | 197 24 979 | 12/1998 |
| EP | 0 329 168 | 8/1989 |
| WO | WO 94/01555 | 1/1994 |

OTHER PUBLICATIONS

The Merck Manual, 14th edition, published by Merck Sharp & Dohme Research Laboratories in 1982, pp 1448–62.*
Rees et al. "Cloning and characterisation of the human 5–HT5A serotonin receptor" FEBS Letters vol. 355 No. 3 (1994) pp. 242–246 (ab only).
Carson et al. "The 5–HT$_{5A}$ Serotonin Receptor is Expressed Predominantly by Astrocytes in which it inhibits cAMP Accumulation: A Mechanism for Neuronal Suppression of Reactive Astrocytes" GLIA No. 17 (1996) pp. 317–326.
Plassat et al. "The mouse 5HT5 receptor reveals a remarkable heterogeneity within the 5HT1D receptor family" The EMBO Journal vol. 11, No. 12 (1992) pp. 4779–4786.
Erlander et al. "Two members of a distinct subfamily of 5–Hydroxytryptamine receptors differentially expressed in rat brain" Proc. Natl. Acad. Sci Vol. 90 No. 8 (1993) pp. 3452–3456 (abstract only).
U.S. patent application Ser. No. 09/869,814, Garcia–Ladona.

* cited by examiner

Primary Examiner—Raymond Henley, III
(74) Attorney, Agent, or Firm—Keil & Weinkauf

(57) ABSTRACT

The invention relates to the use of binding partners for 5-HT5-receptors in the treatment of neuropathological and in particular neurodegenerative and/or neuropsychiatric disturbances which can occur notably in cases of cerebral ishcemia, cerebral stroke, epilepsy and attacks in general, chronic schizophrenia, other psychotic illnesses, dementia, notably Alzheimer's disease, demyelination diseases, notably multiple sclerosis and brain tumors. The invention also relates to methods, especially screening methods, for identifying and characterizing such binding partners.

11 Claims, 4 Drawing Sheets

USE OF 5-HT5-LIGANDS IN THE TREATMENT OF NEURODEGENERATIVE AND NEUROPSYCHIATRIC DISTURBANCES

This application is a 371 of PCT/EP00/00143, filed Jan. 11, 2000.

The present invention relates to the use of binding partners for 5-HT5 receptors for the treatment of neuropathological disorders and associated indications, symptoms and dysfunctions and to processes for the identification and characterization of binding partners of this type.

At least seven different receptor classes mediate the manifold physiological activities which are ascribed to an involvement of the neurotransmitter serotonin (5-hydroxytryptamine, abbreviated 5-HT). According to an internationally recognized classification, they are designated by 5-HT1, 5-HT2, 5-HT3, 5-HT4, 5-HT5, 5-HT6 and 5-HT7. Most of these classes moreover include receptor types which can be differentiated further. Thus the 5-HT1 class includes receptors which can be divided into at least five subclasses, which are designated by 5-HT1A, 5-HT1B, 5-HT1C, 5-HT1D and 5-HT1E (Boess F. G. and Martin I. L., Neuropharmacology 33:275–317 (1994)).

The 5-HT5 class was described for the first time by Plassat et al., The EMBO Journal Vol. 11 No. 13, pp. 4779–4786 (1992). 5-HT5A and 5-HT5B receptors are differentiated (Erlander et al., Proc. Natl. Acad. Sci. USA 90:3452–3456 (1993)). Only small sequence homologies exist between 5-HT5 and other 5-HT receptors. The pharmacological profile of these receptors differs markedly. Using molecular biology techniques, the localization of 5-HT5 receptors was possible in the olfactory bulb, in the hippocampus, in the cortex, in the cerebral ventricles, in the corpus callosum and in the cerebellum. By means of immunohistochemical methods, it was possible to show that 5-HT5 receptors are principally expressed on astrocytes (Carson et al., GLIA 17:317–326 (1996)). Astrocytes are directly adjacent to the basal membrane of brain capillaries of the blood-brain barrier. An abnormal astrocyte endothelium structure accompanies a loss of the blood-brain barrier. The exact significance of the astrocytes is unclear. They appear to look after transport tasks and connective functions. Reactive astrocytes were observed in connection with reactive gliosis in a number of pathological brain changes and neuropsychiatric disorders. As a result of brain injuries, they change their morphologies. The protein expression pattern changes and growth factors are produced. In vitro investigations on cultured astrocytes have allowed the detection of 5-HT5 receptor-mediated responses. It is thus to be suspected on the one hand that they are involved in recovery processes of the brain after disorders, but on the other hand it is also not to be excluded that they contribute to the creation of damage or even to an increase in damage.

CNS disorders nowadays concern large sections of the population. In particular on account of the increase in elderly people, the numbers of patients are increasing continuously. Neuropathological conditions such as cerebral ischemia, stroke, epilepsy and attacks in general, chronic schizophrenia, other psychotic disorders, dementia, in particular Alzheimer's dementia, demyelinizing disorders, in particular multiple sclerosis, and brain tumors lead to damage to the brain and the neuronal deficits associated therewith.

Therapeutic treatments of the neurodegenerative and neuropsychiatric disorders outlined were up to now directed at various membrane receptors with the aim of compensating deficits in neurotransmission processes. Indeed, it was possible to achieve neuroprotective effects with serotonogic compounds in animal models of neuropathological conditions, such as ischemia, cerebral stroke and excitotoxicity. In some cases, it was also possible to observe favorable effects on emotional disturbances, such as depression or anxiety states. Mention may be made here, for example, of 5-HT1A agonists, such as buspirone or the compound 8-hydroxy-2-(di-n-propylamino)tetralin (8-OH-DPAT), which is characterized as a selective 5-HT1A receptor ligand. These active compounds, however, only decrease neurological deficits to a limited extent. There is still no effective therapy at present.

It is therefore an object of the present invention to make possible the treatment of neuropathological disorders with adequate efficacy and minor side effects.

Surprisingly, it has now been found that treatment of the above disease conditions and associated indications, symptoms and dysfunctions is made possible by specific use of substances having binding affinities for 5-HT5 receptors.

One subject of the present invention is therefore the use of binding partners for 5-HT5 receptors for the preparation of an agent for the treatment of neuropathological disorders and associated indications, symptoms and dysfunctions.

Neuropathological disorders are understood according to the invention as meaning disorders which are accompanied by neurological deficits, i.e. a condition characterized by neurological deficiency symptoms. The term "disorder" in the sense according to the invention designates anomalies which, as a rule, are regarded as pathological conditions and can reveal themselves in the form of certain signs, symptoms and/or dysfunctions. The treatment according to the invention can be directed at individual disorders, viz. anomalies or pathological conditions, but a number of anomalies which are causally connected to one another can be combined to give patterns, i.e. syndromes, which can be treated according to the invention.

This condition can exist temporarily, progressively or persistently.

According to the invention, the treatment of neurodegenerative and/or neuropsychiatric disorders is preferred. These disorders occur, in particular, in neuropathological syndromes, as a rule syndromes caused by brain damage, for example cerebral ischemia, stroke, epilepsy and seizures in general, chronic schizophrenia, other psychotic disorders, dementia, in particular Alzheimer dementia, demyelinizing disorders, in particular multiple sclerosis, and brain tumors. The invention in particular also relates to the use of 5-HT5 binding partners for the treatment of those forms of the abovementioned disorders in whose formation and/or course 5-HT5 receptors are involved, i.e. disorders which are modulated by a 5-HT5 receptor activity.

According to a further aspect of the present invention, neuropathological disorders are treated which accompany a glial reaction. The use according to the invention relates in particular to the modulation of a glial reaction.

An advantageous action of the binding partners is seen in the preventive or acute treatment of neurological deficits, which are observed in patients who suffer from psychiatric disorders, such as epilepsy, psychosis, e.g. psychoses of the acute exogenous reaction type or concomitant psychoses of organic or exogenous cause, e.g. after trauma, especially brain lesions and diffuse brain damage, in metabolic disorders, infections, and endocrinopathies; endogenous psychoses, such as schizophrenia, and schizotypic and delusional disorders; effective disorders, such as depression, mania and manic depressive conditions; and mixed forms of the psychoses described above; senile dementia and senile dementia of the Alzheimer type, and in the treatment or prevention of demyelinization processes.

The binding partners according to the invention are efficacious, in particular with respect to the treatment of ischemic damage, e.g. as a result of brain and spinal cord trauma and vascular occlusion or heart failure.

Especially to be mentioned here is stroke (synonym: cerebral apoplexy, cerebral or apoplectic insult, cerebral stroke). Transitory ischemic attacks, reversible ischemic neurological deficits, prolonged reversible ischemic neurological deficits, partially reversible ischemic neurological symptoms and also persistent complete cerebral infarcts can be treated according to the invention. The treatment of acute forms is particularly advantageous according to the invention.

One or more of the changes in nerve tissues listed below underlie the forms of neuropathological disorders which can be preferably treated according to the invention: degeneration or death of neurons, in particular of the ganglial cells, e.g. tigrolysis, indistinctness of the nuclear membrane, plasmolysis, cytoplasm vacuolization and encrustation, parenchymal necroses of the brain, cerebral edema, changes to neurons caused by oxygen deficiency, atrophy, morphological changes, such as demyelinization, in particular medullary sheath disintegration, perivascular infiltrates, glial proliferation and/or glial scarring; degeneration of the Substantia nigra.

The indication to be treated according to the invention is often characterized by a progressive development, i.e. the conditions described above change in the course of time, as a rule the degree of severity increases and conditions further to already existing conditions can occur.

By means of the treatment according to the invention of neuropathological disorders or of the conditions underlying them, a number of further signs, symptoms and/or dysfunctions which are connected with the neuropathological disorders can be treated, i.e. in particular accompany the disorder conditions described above. These include, for example, shock lung, brain nerve losses, e.g. retrobulbar neuritis, eye muscle paralysis, syllabication, spastic paralysis, cerebella symptoms, sensitivity, bladder and rectal disorders, euphoria, dementia, hyper- and akinesia, absence synchynesis, small-step gait, bent posture of trunk and limbs, pro-, retro- and lateropulsion, tremor, lack of facial expression, monotonous speech, depression, apathy, labile or rigid affectivity, impaired spontaneity and resoluteness, slowed thinking, poor association ability; muscular atrophy.

A treatment in the sense according to the invention comprises not only the treatment of acute or chronic signs, symptoms and/or dysfunctions but also a preventive treatment (prophylaxis), in particular as a relapse or phase prophylaxis. The treatment can be achieved symptomatically, for example as symptom suppression. It can be carried out short-term, be carried our medium-term, or it can also be a long-term treatment, for example in the context of a maintenance therapy.

The term "binding partner for 5-HT5 receptors" describes substances which bind to 5-HT5 receptors and can therefore also be designated as 5-HT5 receptor ligands.

Binding is understood as meaning any molecular interaction between the binding partner and the receptor, in particular under physiological conditions. As a rule, these are conventional interactions, which include electrostatic attraction, hydrogen bonding, hydrophobic bonds, van-der-Waals forces or metal complex-like coordinative bonds. In addition to the abovementioned, reversible molecular interactions, irreversible interactions between binding partner and receptor can also be possible, such as, for example, covalent bonds.

According to one embodiment, binding partners which can be used according to the invention competitively inhibit the binding of comparison binding partners, such as 5-HT (5-hydroxytryptamine) or 5-CT (5-carboxamidotryptamine), to 5-HT5 receptors.

Competitive inhibition is understood as meaning that binding partners which can be used according to the invention compete with a comparison binding partner, in the present case, for example, 5-HT or 5-CT, for binding to the receptor, i.e. the binding of one prevents the binding of the other.

According to a further embodiment, binding partners which can be used according to the invention inhibit the binding of comparison binding partners, such as 5-HT (5-hydroxytryptamine) or 5-CT (5-carboxamidotryptamine) to 5-HT5 receptors noncompetitively.

Noncompetitive inhibition is understood as meaning that binding partners which can be used according to the invention modulate, via their binding to the receptor, the binding of a comparison binding partner, in the present case, for example, 5-HT or 5-CT, in particular lower its binding affinity.

At least in the case of competitive inhibition, i.e. of reversible binding, the principle applies that the displacement of one binding partner by another increases with decreasing binding affinity of the one or increasing binding affinity of the other with respect to the receptor. More expediently, therefore, binding partners which can be used according to the invention have a high binding affinity for 5-HT5 receptors. A binding affinity of this type allows, on the one hand, an effective displacement of naturally occurring binding partners for 5-HT5 receptors, such as, for example, serotonin (5-hydroxytryptamine, 5-HT) itself, where the necessary concentration of binding partner which can be used according to the invention for the binding of a certain amount of this binding partner to 5-HT5 receptors decreases with increasing binding affinity. With respect to medical use, binding partners are therefore preferred whose binding affinity is so great that these can be administered in justifiable amounts in the course of an effective medical treatment as an active compound. Binding partners which can be used according to the invention are therefore preferably administered in daily doses of approximately 0.01 to 100 mg/kg of body weight and in particular of approximately 0.1 to 15 mg/kg of body weight on parenteral administration and 1 to 30 mg/kg of body weight on oral administration.

The competition experiments referred to above, with which that concentration of binding partner which can be used according to the invention is determined in vitro which displaces 50% of another comparison binding partner from the receptor binding site ($IC_{50}$ values), offer one possibility of expressing the binding affinity. Thus the competitive inhibition of the binding of 5-CT to 5-HT5 receptors can also be evaluated to the effect that binding partners which can preferably be used according to the invention have half-maximal inhibition constants $IC_{50}$ of less than $10^{-5}$ M, preferably of less than $10^{-6}$ M and in particular of less than $10^{-7}$ M.

The binding affinity of binding partners which can be used according to the invention can also be expressed by means of the inhibition constant $K_i$, which is in general likewise determined in vitro using competition experiments. For the binding of 5-HT5 receptors, binding partners which can be used according to the invention preferably have $K_i$ values of less than $10^{-6}$ M, advantageously of less than $10^{-7}$ M and particularly preferably of less than $10^{-8}$ M. $K_i$ values of compounds which can be used according to the invention lie, for example, in the range from $1 \cdot 10^{-7}$ M to $7 \cdot 10^{-7}$ M or in the range from $1 \cdot 10^{-8}$ M to $1 \cdot 10^{-7}$ M.

Binding partners which can be used can bind with a lower, an essentially identical, or a higher affinity to 5-HT5 than to a specific receptor which is different from 5-HT5.

Thus binding partners for 5-HT5 receptors with respect to the use according to the invention in particular include those whose binding affinity for 5-HT5 receptors compared with the affinity for 5-HT1 receptors, in particular 5-HT1A, 5-HT1B and/or 5-HT1D, is so high that they are advantageously suitable for the use according to the invention. This does not necessarily presuppose a comparatively more selective binding to 5-HT5 receptors, even though selective binding partners for 5-HT5 receptors are a particular embodiment of the present invention.

For example, binding partners can be used which have high affinity both for 5-HT5 and for 5-HT1 receptors, in particular for 5-HT1A, 5-HT1B and/or 5-HT1D. In this connection, high affinity means $K_i$ values as a rule in the range from $1 \cdot 10^{-9}$ M to $1 \cdot 10^{-6}$ M. According to a particular embodiment, binding partners which can be used in the high affinity range have a binding profile for 5-HT receptors which is characterized by a binding affinity to 5-HT5 which, in comparison to other binding affinities of this range is essentially identical or only slightly less. Factors of 10 or less can be advantageous.

Selective binding partners which can be used according to the invention have binding affinities for 5-HT5 receptors which are larger than for one or more 5-HT receptors which are different from 5-HT5, i.e. in particular receptors allocated to the abovementioned 5-HT receptor classes 5-HT1, 5-HT2, 5-HT3, 5-HT4, 5-HT6 and 5-HT7. If the binding affinity for 5-HT5 receptors of a binding partner is greater than that of a 5-HT receptor which is different from 5-HT5, we speak of a selective binding of these binding partners to 5-HT5 receptors in relationship to the 5-HT receptor which is different from 5-HT5. Particular binding partners are those whose binding affinity for 5-HT5 receptors is greater than for at least one and in particular all 5-HT1 receptors, in particular for 5-HT1A, 5-HT1D and/or 5-HT1B receptors. Binding partners whose binding affinity for 5-HT5 receptors is greater than for all 5-HT receptors which are different from 5-HT5 constitute a further particular class of binding partners according to the invention.

Selectivity is understood as meaning the property of a binding partner to bind preferably to 5-HT5 receptors.

It is decisive for the selectivity outlined above that the binding affinities for 5-HT5 receptors on the one hand and for one or more 5-HT receptors which are different from 5-HT5 on the other hand are adequately different. Affinity differences are preferred according to which binding affinity ratios of at least 2, advantageously of at least 5, particularly advantageously of at least 10, preferably of at least 20, particularly preferably of at least 50 and in particular of at least 100 are present.

According to a further embodiment, binding partners which can be used according to the invention bind selectively to 5-HT5 receptors having the advantageous binding affinities described above in relation to one or more 5-HT receptors other than 5-HT5.

According to a further embodiment, binding partners which can be used according to the invention bind selectively to 5-HT5 receptors having the advantageous binding affinities described above in relation to all 5-HT receptors other than 5-HT5.

Binding partners are particularly advantageous which bind to 5-HT5 receptors which are expressed by glia cells and in particular by astrocytes with the affinities and selectivities described above.

According to the invention, the human receptor variant is a preferred target for the binding partners employed according to the invention.

The binding of binding partners according to the invention to 5-HT5 receptors is coupled to an effector function. Binding partners can act agonistically or antagonistically and partly agonistically and/or partly antagonistically.

Agonists are designated as compounds according to the invention which completely or partially imitate the activity of 5-HT on 5-HT5 receptors.

Antagonists are designated as compounds according to the invention which can block the agonistic activity of 5-HT on 5-HT5 receptors.

According to a preferred embodiment of the present invention, binding partners are employed whose binding at least to 5-HT5 receptors of h5-HT5-transfected CHO cells brings about a change in the agonist-induced stimulation of GTP binding to membrane-bound G proteins, a change in intracellular calcium levels, a change in agonist-induced induction of phospholipase C activity and/or a change in cAMP production. As far as the change in intracellular calcium levels is concerned, the use of binding partners which bring about an increase in intracellular calcium levels represents a particular embodiment of the invention.

This embodiment also includes binding partners which are active in known animal models for neurodegenerative and neuropsychiatric processes.

Preferred binding partners are those which are also selective for 5-HT5 receptors in relation to their effector function in the sense described above.

Compounds which can be used according to the invention are described, for example, in DE 197 24 979.5. These are 3-substituted 3,4,5,6,7,8-hexahydropyrido[3', 4':4,5]thieno-[2,3-d]pyrimidine derivatives of the formula I

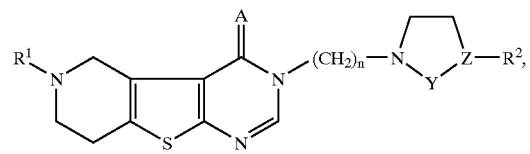

in which

R$^1$ is a hydrogen atom, a $C_1$–$C_4$-alkyl group, an acetyl group, a phenylalkyl $C_1$–$C_4$ radical, where the aromatic is optionally substituted by halogen, $C_1$–$C_4$-alkyl, trifluoromethyl, hydroxyl, $C_1$–$C_4$-alkoxy, amino, cyano or nitro groups or is a phenylalkanone radical, where the phenyl group can be substituted by halogen, R$^2$ is a phenyl, pyridyl, pyrimidinyl or pyrazinyl group, which is optionally mono- or disubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups, and which can optionally be fused to a benzene nucleus, which can optionally be mono- or disubstituted by halogen atoms, $C_1$–$C_4$-alkyl, hydroxyl, trifluoromethyl, $C_1$–$C_4$-alkoxy, amino, cyano or nitro groups and can optionally contain 1 nitrogen atom, or to a 5- or 6-membered ring which can contain 1–2 oxygen atoms, A is NH or an oxygen atom,
Y is $CH_2$, $CH_2$—$CH_2$, $CH_2$—$CH_2$—$CH_2$ or $CH_2$—CH,
Z is a nitrogen atom, carbon atom or CH, where the bond between Y and Z can also be a double bond,
and n is the number 2, 3 or 4
and their salts with physiologically tolerable acids.

Further compounds which can be used according to the invention are described, for example, in DE 196 36 769.7. These are 3-substituted 3,4,5,6,7,8-hexahydropyrido[4',3':4,5]thieno-[2,3-d]pyrimidine derivatives of the formula I

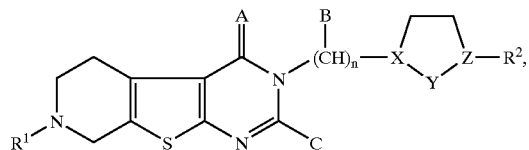

in which
R$^1$ is a hydrogen atom, a $C_1$–$C_4$-alkyl group, an acetyl or benzoyl group, a phenyl $C_1$–$C_4$-alkyl radical, where the aromatic is optionally substituted by halogen, $C_1$–$C_4$-alkyl, trifluoromethyl, hydroxyl, $C_1$–$C_4$-alkoxy, amino, cyano or nitro groups, or is a naphthyl-$C_1$–$C_3$-alkyl radical, a phenyl-$C_2$–$C_3$-alkanone radical or a phenylcarbamoyl-$C_2$-alkyl radical, where the phenyl group can be substituted by halogen,
R$^2$ is a phenyl, pyridyl, pyrimidinyl or pyrazinyl group, which is optionally mono-, di- or trisubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups, and which can optionally be fused to a benzene nucleus which can optionally be mono- or disubstituted by halogen atoms, $C_1$–$C_4$-alkyl, hydroxyl, trifluoromethyl, $C_1$–$C_4$-alkoxy, amino, cyano or nitro groups and can optionally contain 1 nitrogen atom, or to a 5- or 6-membered ring which can contain 1–2 oxygen atoms,
or can be substituted by a phenyl-$C_1$–$C_2$-alkyl or -alkoxy group, where the phenyl radical can be substituted by halogen, or a methyl, trifluoromethyl or methoxy group,
A is NH or an oxygen atom,
B is hydrogen or methyl,
C is hydrogen, methyl or hydroxyl,
X is a nitrogen atom,
Y is $CH_2$, $CH_2$—$CH_2$, $CH_2$—$CH_2$—$CH_2$ or $CH_2$—CH,
Z is a nitrogen atom, carbon atom or CH, where the bond between Y and Z can also be a double bond,
and n is the number 2, 3 or 4,
and their salts with physiologically tolerable acids.

5-HT5-specific antibodies can also be utilizable as 5-HT5 binding partners. They can be polyclonal antisera, monoclonal antibodies, antibody fragments, such as F(ab), Fc, etc., chimeric and recombinant antibodies. Such antibodies can be prepared in a manner known per se. As an immunogen, 5-HT5 receptor can be used as such or antigenic fragments thereof, as a rule coupled to customary carrier proteins.

Further low molecular weight 5-HT5 binding partners, usually synthetic compounds, can be used advantageously in many respects.

Aptamers, i.e. nucleic acids, as a rule oligonucleotides, having sufficient affinity for 5-HT5 receptors, can also be used as binding partners.

The use according to the invention is not restricted to the abovementioned binding partners. Rather, any substance which binds to 5-HT5 receptors in the manner described above, can be used according to the invention as a 5-HT5 binding partner.

Assays for the determination of binding affinities of test substances for 5-HT5 receptors are known in principle. This can be carried out, for example, by assessing the competitive inhibition of the binding of a comparison binding partner to 5-HT5 receptors by the substance to be investigated. Suitable comparison binding partners are known ligands for 5-HT receptors, such as 5-HT or 5-CT or LSD. These are expediently labeled such that their binding to 5-HT receptors can be monitored analytically using standard methods. Radioactive and optical markers are preferred. In binding studies on 5-HT5 receptors, according to the invention, 5-CT or LSD, in particular in the form of [$^3$H]-LSD, is used. The binding affinities can be expressed as half-maximal inhibition constants $IC_{50}$ or as inhibition constants $K_i$. This process is preferably used for primary screening. SPA technology or FlashPlate technology is preferably used.

The binding to binding partners to be investigated can also be determined directly on 5-HT receptors. The inhibition constants $K_i$ expressing binding affinity can be determined, for example, calorimetrically, i.e. by measurement of the binding energy released.

Effector functions can also be assessed qualitatively or quantitatively both in vitro and in vivo with the aid of known functional assays.

The assessment of an agonistic activity can be based on all those effects which are produced by the binding of 5-HT to 5-HT5 receptors. It is preferred according to the invention to assess the effects on the binding of GTP to G proteins, on intercellular calcium levels, on the phospholipase C activity and/or on the cAMP production. These processes are preferably used for secondary screening. Here too, SPA or FlashPlate technology is advantageously used.

GTP binding to G proteins can be investigated by using a nonhydrolyzable analog of GTP, for example [$^{35}$S]GTPγS, whose binding can be investigated radiologically. This investigation is preferably carried out on membranes having 5-HT5 receptors.

For the measurement of intracellular calcium levels, it is possible to employ suitable calcium probes, as a rule calcium chelating agents, for example fluorescing compounds, such as Fura 2-acetylmethyl ester or fluo-3-AM. This investigation is preferably carried out on cell cultures having 5-HT5 receptors, in particular on individual cells.

The phospholipase C activity can be determined by means of the reactions catalyzed by it, for example, the incorporation of myoinositol, which for detection purposes is preferably radiolabeled as [$^3$H]-myoinositol, or the conversion of $PPIP_2$ to $IP_3$, where the $PPIP_2$ is also preferably radiolabeled as [$^{32}$P]$PIP_2$. These investigations are preferably carried out on individual cells having 5-HT5 receptors.

cAMP production can be determined with the aid of the cAMP binding protein. This investigation is preferably carried out on individual cells having 5-HT5 receptors.

If appropriate, the effector function is also determined, i.e. the activity of binding partners according to the invention for other 5-HT receptors. This expediently takes place taking into account the binding affinities determined for 5-HT5 and other 5-HT receptors, i.e. in particular taking into account the selectivity.

The present invention therefore also relates to processes for the identification and characterization of binding partners which can be used according to the invention. These and further processes which are similarly suitable can form the basis for in vitro screening processes with which it is possible from a large number of different compounds to pick out those which, with respect to future use, appear to be the most promising. For example, by means of combinatorial chemistry, extensive substance banks can be prepared which comprise myriads of potential active compounds. The inspection of combinatorial substance libraries for substances having desired activity is automatable. Screening robots are used for the efficient evaluation of the individual assays, which are preferably arranged on microtiter plates. Thus the present invention also relates to screening processes, i.e. both primary and secondary screening processes, in which preferably at least one of the processes described below is used. If a number of processes are used, this can be shifted in terms of time or simultaneously carried out on one and the same sample or on different samples of a substance to be investigated.

A particularly effective technology for carrying out processes of this type is the scintillation proximity assay, called SPA for short, known in the field of active compound screening. Kits and components for carrying out this assay can be obtained commercially, for example from Amersham Pharmacia Biotech. In principle, solubilized or membrane-bound receptors are immobilized on small fluoromicrospheres containing scintillation substance. If, for example, a radioligand binds to the immobilized receptors, the scintillation substance is stimulated to emit light, since the spatial vicinity between scintillation substance and radioligand is specified.

A further particularly effective technology for carrying out processes of this type is the FlashPlate® technology known in the field of active compound screening. Kits and components for carrying out this assay can be obtained commercially, for example from NEN® Life Science Products. This principle is likewise based on microtiter plates (96-well or 384-well), which are coated with scintillation substance.

The abovementioned assays are known in principle to the person skilled in the art.

Figure 1:
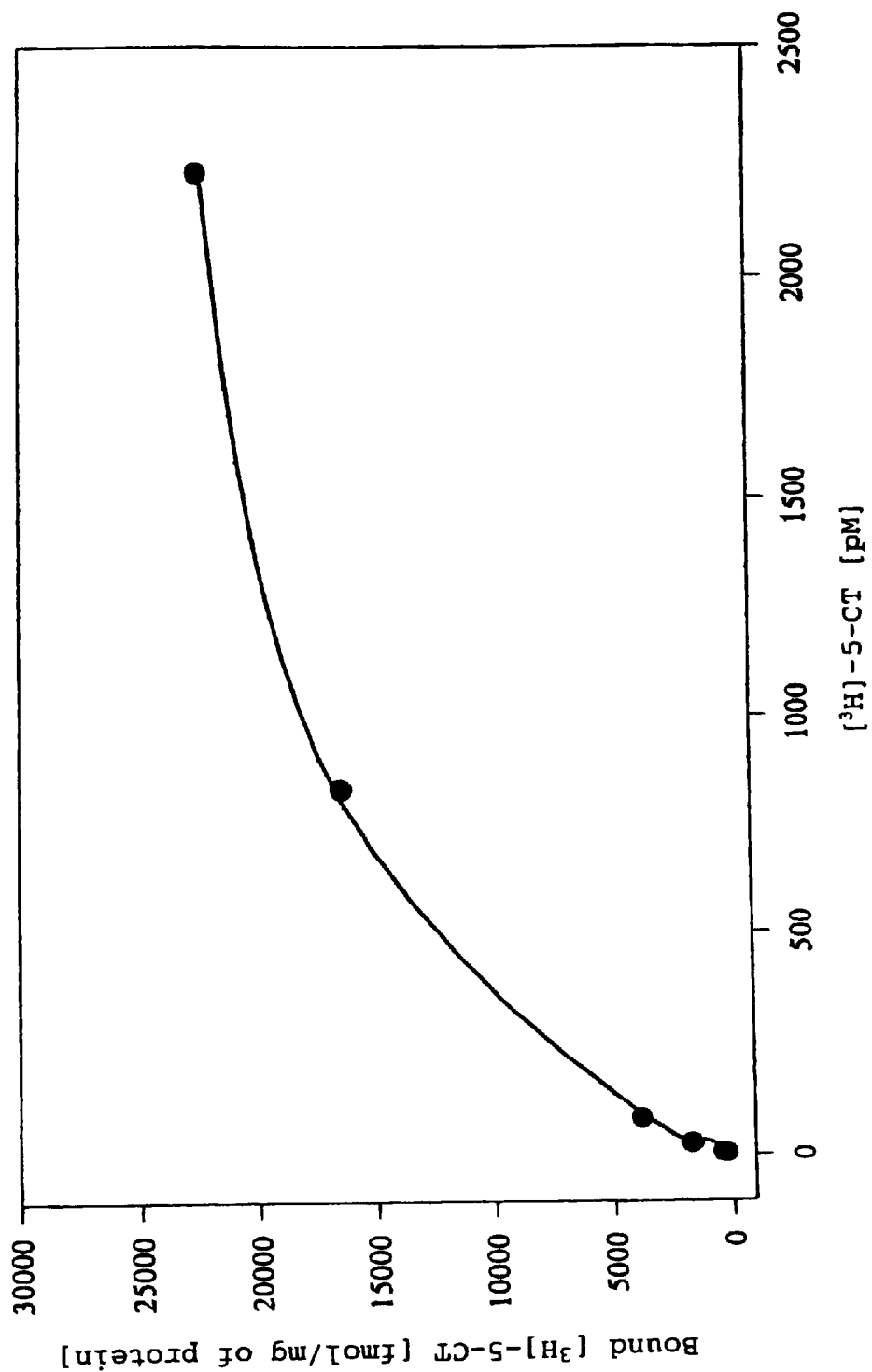
FIG. 1 shows the concentration of bound [$^3$H]-5-CT in relation to [$^3$H]-5-CT.

A first process according to the invention is used for the determination of the affinity and/or selectivity of binding partners for 5-HT5 receptors. For this purpose, the binding partner is brought into contact with 5-HT5 receptors and the binding affinity is determined.

For the determination of selectivities, the binding affinity of the binding partner to be investigated to other 5-HT receptors is determined in the same manner—if appropriate using the ligands specific for the respective receptor—and the values obtained are compared.

A further process according to the invention relates to the determination of the activity of binding partners for 5-HT5 receptors, i.e. the determination of agonistic, partly agonistic, antagonistic and/or partly antagonistic action. For this purpose, the binding partner is brought into contact with 5-HT5 receptors and the effects caused by the binding are assessed.

According to a preferred embodiment, binding partners are subjected to a primary screening by determining their binding affinity to 5-HT5 receptors using the [$^3$H]-5-CT or [$^3$H]-LSD competition experiment described above. Those binding partners which have an inhibition constant IC$_{50}$ in the range of $10^{-6}$ M or less are then subjected to a secondary screening by assessing their effector function in the manner described above, in particular with respect to GTP binding and/or the intracellular calcium levels. Finally, the binding partners selected in this way can be subjected to a counter-screening for selectivity determination by determining their binding affinity to further 5-HT receptors essentially in the manner described above—but optionally using the ligands specific to the respective receptors. For example, [$^3$H]-8-hydroxydipropylaminotetralin ([$^3$H]-8-DPAT) can be used for binding studies to 5-HT1A receptors, while 5-HT1B and 5-HT1D receptors can be investigated using [$^3$H]-5-CT.

5-HT5 receptors are preferably made available in the form of cellular systems, i.e. in the form of membranes, cells, cell colonies, tissues or organs which carry 5-HT5 receptors. Cellular systems of this type can express 5-HT5 receptors by nature, but they can also be induced to express 5-HT5 by suitable genetic manipulation, e.g. by transfection. In the context of the preferred embodiment of the present invention concerning h5-HT5, it is possible to use for this purpose, in particular, the coding sequence described in Rees S. et al, FEBS Letters 335:242–246 (1994) (accession number X81411). Human glioma cell lines are preferred as natural cellular systems having 5-HT5 receptors. Of the h5-HT5-transfected heterologous cell lines, those are preferred which express the h5-HT5 gene. Mention may be made, for example, of h5-HT5-transfected CHO cells, h5-HT5-transfected human kidney cells, in particular h5-HT5-transfected HEK293 cells, or h5-HT5-transfected C-6 glioma cells.

For the determination of selectivity, affinity and activity of binding partners according to the invention, it is also possible to use brain tissue sections and native membranes from brain parts. If radio labels are employed, the assessment of tissue sections is preferably carried out autoradiographically.

The neuroprotective action is preferably determined on animal models of neurodegenerative and neuropsychiatric processes.

Preferred animal models are those for cerebral stroke and cerebral disorders in the case of multiple infarct, for example cerebral ischemias as a result of an occlusion of the carotid artery or the middle cerebral artery (MCA occlusion), fore brain ischemias and hypoxia tolerance tests, anxiolytic models, for example active compound-induced convulsions, electroshock- or isolation-induced aggression, models of antiepileptic activity, for example electroshock-, active compound- or noise-induced attacks and genetic models, excitotoxic neurodegeneration models and demyelinization models.

In the context of the treatment, the use according to the invention of 5-HT5 binding partners comprises a process. In this process, the individual to be treated, preferably a mammal, in particular a human, agricultural or domestic animal, is administered an efficacious amount of one or more 5-HT5 binding partners, as a rule corresponding to pharmaceutical and veterinary medical practice. Whether such a treatment is indicated and in what form it has to take place depends on the individual case and is subject to medical assessment (diagnosis), the signs, symptoms and/or dysfunctions present, risks of developing certain signs, symptoms and/or dysfunctions, and additionally includes further factors.

As rule, the treatment is carried out by single or repeated daily administration, if appropriate together or in alternation with other active compounds or active compound-containing preparations, such that an individual to be treated is administered a daily dose of approximately 0.001 g to 10 g, preferably of approximately 0.001 g to approximately 1 g.

The invention also relates to the preparation of pharmaceutical compositions for the treatment of an individual, preferably a mammal, in particular a human, agricultural or domestic animal. The binding partners according to the invention are usually administered in the form of pharmaceutical compositions which comprise a pharmaceutically tolerable excipient with at least one inhibitor according to the invention and, if appropriate, further active compounds. These compositions can be administered, for example, by the oral, rectal, transdermal, subcutaneous, intravenous, intramuscular or intranasal route.

Examples of suitable pharmaceutical formulations are solid pharmaceutical forms, such as powders, granules, tablets, pastilles, sachets, cachets, coated tablets, capsules such as hard and soft gelatin capsules, suppositories or vaginal pharmaceutical forms, semisolid pharmaceutical forms, such as ointments, creams, hydrogels, pastes or patches, and also liquid pharmaceutical forms, such as solutions, emulsions, in particular oil-in-water emulsions, suspensions, for example lotions, injection and infusion preparations, eye and ear drops. Implanted delivery devices can also be used for the administration of binding partners according to the invention. In addition, liposomes, microspheres or polymer matrices can also be used.

In the production of the compositions, binding partners according to the invention are usually mixed or diluted with an excipient. Excipients can be solid, semisolid or liquid materials which are used as a vehicle or medium for the active compound.

Suitable excipients include, for example, lactose, dextrose, sucrose, sorbitol, mannitol, starches, acacia gum, calcium phosphate, alginates, tragacanth, gelatin, calcium silicate, microcrystalline cellulose, polyvinylpyrrolidone, cellulose, water, syrup and methylcellulose. In addition, the formulations can comprise pharmaceutically acceptable vehicles or customary excipients, such as lubricants, for example tallow, magnesium stearate and mineral oil; wetting agents; emulsifying and suspending agents; preservatives, such as methyl and propyl hydroxybenzoates; antioxidants; antiirritants; chelating agents; pan-coating auxiliaries; emulsion stabilizers; film-forming agents; gel-forming agents; flavor-masking agents; flavor corrigents; resins; hydrocolloids; solvents; solubilizers; neutralizing agents; permeation accelerators; pigments; quaternary ammonium compounds; refatting and superfatting agents; ointment, cream or oil bases; silicone derivatives; spreading auxiliaries; stabilizers; sterilizing agents; suppository bases; tablet excipients, such as binders, fillers, lubricants, disintegrants or coatings; propellants; drying agents; opacifying agents; thickeners; waxes; plasticizers; white oils. A relevant embodiment is based on expert knowledge, such as is presented, for example, in Fiedler, H. P., Lexikon der Hilfsstoffe für Pharmazie, Kosmetik und angrenzende Gebiete [Encyclopedia of excipients for pharmacy, cosmetics and related areas], 4th Edition, Aulendorf: ECV-Editio-Kantor-Verlag, 1996.

The present invention is illustrated in greater detail by means of the following examples, without being restricted thereto.

REFERENCE EXAMPLE 1 h5-HT5 Receptor-expressing HEK293 Cells and CHO Cells

The gene coding for the human 5-HT5 receptor was isolated from human tissues in a known manner by means of 3'-5'-RT-PCR (RACE system, Boehringer Mannheim). The gene sequence was then inserted into a plasmid carrying the neomycin resistance gene (pcDNA3; Invitrogen, Germany) and amplified in $E.$ $coli$ according to the manufacturer's instructions. A preparation of the resulting plasmid was mixed with Lipofectamin® (Gibco Life-Sciences, Germany), and HEK293 cells were incubated with a thin layer of this transfection mixture in petri dishes (2.5 cm). The transfection mixture was then replaced by neomycin-containing culture medium. Surviving cells were further cultured in DMEM-F12 medium which was supplemented with 10% fetal calf serum, 2 mM glutamine and antibiotics (90 mg of streptomycin, 90 mg of penicillin). The cells were grown to confluence under 5% $CO_2$, 95% atmospheric humidity and 37° C.

h5-HT5 Receptor-expressing CHO Cells are Obtained Analogously.

REFERENCE EXAMPLE 2

Cell Membrane Preparation

The method used here essentially follows known methods for the preparation of cell membranes from cells (Findlay J. B. C. and Evans W. H. Biological Membranes, Practical Approach (1987)). The cells cultured according to Reference Example 1 were carefully scraped off the surface of the culture vessel and centrifuged in DMEM-F12 medium at 180×g for 10 min. The cell pellets obtained were resuspended in 5 mM tris HCl buffer containing 5 mM EDTA, 5 mM EGTA, 0.1 mM PMSF and 3 mM benzamidine (pH: 7.6; buffer A) and incubated at 4° C. for 15 min. The cell suspension was homogenized (6×3s) in an Ultraturrax® (15,000 rpm) and centrifuged at 1000×g and 4° C. for 1 min. The pellet was resuspended in buffer A and, as described above, homogenized and centrifuged. The supernatants from both steps were collected and centrifuged at 40,000×g and 4° C. for 20 min. The pellet was resuspended and homogenized in buffer A (1×15s). The membrane suspension was centrifuged at 40,000×g and 4° C. for 20 min. The resulting pellet was resuspended in buffer A containing 10% glycerol and 1% bovine serum albumin. Aliquots were frozen and stored at −80° C. until use.

REFERENCE EXAMPLE 3

Kinetics of the Saturation Binding of [$^3$H]-5-CT

The methodology is essentially known (Ress S. et al., FEBS Letters 335:242–246 (1994)). Membranes obtained according to Reference Example 2 (200 $\mu$l) were incubated in a total volume of 600 $\mu$l in 100 mM tris-HCl containing 1 mM EDTA (pH: 7.7; buffer B) with increasing concentrations of [$^3$H]-5-CT (96 Ci/mmol), 10 $\mu$M methiothepine being added for the determination of the specific binding, while methiothepine was not added for the determination of the total binding. The mixture was incubated at 30° C. for 90 min. The samples were then filtered, a SkatronR filtration system and GF/B filters embedded in 0.3% polyethyleneimide being used. The filters were washed at 4° C. with 9 ml of buffer B. The radioactivity retained on the filters was measured by means of liquid scintillation counting, 5 ml of Ultima-Gold (Packard) being used.

REFERENCE EXAMPLE 4 a) [³H]-5-CT Binding Competition

The experiments on binding competition were carried out essentially following known investigations (Rees et al., 1994). Membranes obtained according to Example 2 (200 µl) were incubated in the presence of 2 nM [³H]-5-CT in a total volume of 600 µl in buffer B with increasing concentrations of selected compounds. After an incubation time of 75 min at 30° C., the samples were filtered at 4° C. through GF/B filters embedded in 0.3% polyethyleneimine using buffer B. The filters were washed with 9 ml of buffer B. The radioactivity retained on the filters was determined as in Reference Example 3. The total binding was defined as that binding of the radioligand which was observed without addition of further compounds. This nonspecific binding was defined as that binding of [³H]-5-CT which was observed in the presence of 10 µM methiothepine. Similar systems can also be used which, as a result of use of microtiter plates, allow a high sample throughput and secondary screening.

The saturation parameters of the [³H]-5-CT binding was determined both by nonlinear regression analysis and from linear plots using the SigmaPlot software (Jandel Scientific, Germany). Competition curves were set up in which the radioactive binding is expressed as a percentage proportion of the total binding. Half maximal inhibition constants $IC_{50}$ and Hill-coefficients ($n_H$) were determined by means of nonlinear regression analysis.

b) Identification of h5-HT5 Receptor Ligands by HTS Using FlashPlate Technology.

96-well FlashPlates which are coated with h5-HT5 membranes can be obtained from Bio Signal Inc. (Canada). [3H]-LSD was diluted to a suitable concentration in Tris HCl buffer which contains 10 mM $MgCl_2$, 0.5 mM EDTA and 0.5% of BSA. The radioligand solution was added to the wells (25 ml), which either contained or did not contain test compound. The plates were incubated at room temperature for 180 minutes and the radioactive signal was measured using a micro β-counter (Wallac). The nonspecific binding was determined using methiothepine. [3H]-LSD has an affinity of 12 nM. With increasing binding affinity of the test compound, the radioactive signal of [3H]-LSD decreased.

REFERENCE EXAMPLE 5

Determination of the Agonist-induced Stimulation of [³⁵S] GTPγS Binding

[³⁵S]GTPγS binding assays are known. The present assay was carried out following the previously described method of Hilf, G. and Jakobs, K. H. (Eur. J. Mol. Pharmacol. 225:245–252 (1992)). Active compound-induced changes in the [³⁵S]GTPγS binding to membranes of HEK293 cells stably transfected with the h5-HT5 receptor gene were measured (see Reference Examples 1 and 2). The cell membranes (12 µg) were incubated with 50 mM triethanolamine HCl buffer (pH: 7.5) containing 6.75 mM $MgCl_2$, 150 mM NaCl, 1 mM DTT, 1 mM EDTA, 10 µM GDP and [³⁵S]GTPγS. Following a 60-minute incubation at 30° C. with or without addition of the active compounds to be tested, the test mixture (100 µl) was rapidly filtered through GF-B filters using a Skatron® filtration device. The filters were rapidly washed with 50 mM tris HCl buffer (9 ml; pH: 7.5; 4° C.) containing 1000 mM NaCl and 5 mM $MgCl_2$. The radioactivity retained on the filters was determined by means of scintillation spectrometry, Ultima Gold scintillation fluid being used. Similar systems which allow a high throughput and secondary screening as a result of use of microtiter plates can likewise be used.

The active compound activities were expressed as a percentage proportion of the basic binding measured in the absence of the active compound. The matching of the curves was carried out using software for nonlinear regression analysis (SigmaPlot, Jandel Scientific, Germany) according to the general equation $E=(L \times E_{max})/(L+EC_{50})$, in which E is the action, L is the ligand concentration, $E_{max}$ is the maximum action and $EC_{50}$ is that concentration which induces 50% of the maximal action.

REFERENCE EXAMPLE 6

Determination of Agonist-induced Changes of Intracellular Calcium Levels

The method is known (Kao J. P. Y. Methods in Cell Biology 40:155–181 (1994)). As described in Reference Example 1, h5-HT5 receptor-expressing HEK293 cells were grown in culture vessels. The cells were carefully scraped off before they were confluent. The cells were labeled with Fura 2 by incubating at room temperature with Fura 2-acetylmethyl ester (Sigma). The cells ere centrifuged at 180×g for 10 min and resuspended in DMEM-F12 medium without serum and incubated at 37° C., 5% $CO_2$ and 95% atmospheric humidity for 45 min.

Intracellular calcium levels were determined with a fluorescence microscope which was equipped with a suitable filter exchange system (Olympus/Hamamatsu). The fluorescence ratio (340 nm/380 nm) was determined using the Argus® software. The intracellular calcium levels were observed for a short time in individual cells without the addition of active compounds and hen 30 min after addition of the active compound to be tested. Similar systems which permitted a high throughput and secondary screening as a result of the use of microtiter plates could likewise be used.

The modulation of intracellular $Ca^{2+}$ levels can be assessed analogously in HTS. For this, h5-HT5 receptor-expressing CHO cells were cultured overnight in 96-well plates (30,0000 [sic]–80,000 cells/well). The cells were labeled for one hour using HEPES buffer containing 1 mM Fluo-3-AM, 10% pluronic acid and 2.5 mM probencid, and washed. A test compound was added to each well. For the determination of the calcium levels, the fluorescence intensity was read off using a fluorometrically operating plate reader (Fluorometric Imaging Plate Reader; FLIPR).

REFERENCE EXAMPLE 7

Determination of the Agonist-induced Phospholipase C Activity

The method is essentially known (Garcia-Ladona F. J. et al., Neuroreport 4:691–694 (1993)). The cells were incubated with 0.125 µM [³H]myoinositol for 24 h. Unincorporated [³H]myoinositol was removed from the medium and replaced by Krebs-Henseleit buffer containing 10 mM LiCl. After incubation for 10 minutes, the active compound to be tested was added. After 45 min, the reaction was stopped by replacing the stimulation medium by distilled water. If tissue samples are used, a similar procedure is employed (Garcia-Ladona et al., 1993). The cells were frozen and stored at −80° C. The production of [³H]inositol monophosphate was determined by means of known chromatographic methods. A similar method can be used with tissue miniprisms. The determination of the phospholipase C stimulation was likewise carried out in a similar manner by preparing membrane fractions, as described in Reference Example 2, and incubating with [³²P]PIP₂ and active compounds. In this case, the production of IP3 was determined. Known processes were also optimized in order to use systems based on microtiter plates. Commercially obtainable materials allow extension to analyses with a high throughput and the carrying-out of secondary screening.

REFERENCE EXAMPLE 8
Determination of the Agonist-induced Change in cAMP Production The method used is essentially known (Strada S. S. et al., Methods in Neurotransmission receptor analysis: 89–110 (1990)). Cells were incubated in culture medium without serum and antibiotics for 10 min. The medium was heated at 95° C. for 15 min in order to stop the reaction. The cell samples were frozen and stored at −80° C. cAMP levels were determined using commercially obtainable kits which use the cAMP binding protein. Known processes were also optimized in order to use systems based on microtiter plates. Commercially obtainable materials allow extension to analyses with a high throughput and the carrying-out of secondary screening.

REFERENCE EXAMPLE 9
Tissue Preparation 90 min after administration of the active compound (orally, intraperitoneally, intravenously or intracerebroventricularly), the experimental animals were decapitated. The entire brain was rapidly removed from the skull, frozen on dry ice and stored at −80° C. Rat brain sections (15 $\mu$m) were obtained in a cryostat at −20° C., applied to gelatin-coated slides and stored at −30° C. until use.

REFERENCE EXAMPLE 10
Neuroprotective Action: MCA Occlusion

The neuroprotective activity of the test compounds was investigated for experimentally caused cerebral stroke in a standard model. The experiments were performed on male Long Evans rats. Under nitrous oxide-assisted halothane anesthesia, the middle cerebral artery (MCA) was severed and permanently ligated distally, as described in the literature. The resulting infarct volume was determined 22 hours after MCA occlusion.

REFERENCE EXAMPLE 11
Neuroprotective Action: Experimental Brain Trauma of the Rat The lateral fluid percussion method (McIntosh TK, Neuroscience 28, 233 244, 1989) was used in order to produce an experimental brain trauma in the rat which is suitable for the testing of potential neuroprotective substances. By means of this technique, controlled and consistent tissue damage was produced underneath the site of the impact, which included the neocortex, the hippocampus and the thalamus.

The right parietotemporal region of the skull was exposed in the anesthetized rat. The skull was trepanned through the parietal cortex (about 4 mm diameter), the dura being left intact. A Luer lock attachment was fixed to the skull using dental cement through the trepanation. After the dental cement had hardened, the rat was connected to the fluid percussion apparatus according to McIntosh. This consisted of a cylinder filled with 0.9% NaCl solution, one end of the cylinder being closed by a piston, while the other end was connected via a pressure transducer to a Luer lock attachment. Using this, the counterpart on the rat was tightly closed so that a liquid column was formed adjacent to the dura. A metal pendulum was allowed to impact onto the piston from a predetermined height so that a brief blow of the compressed liquid column on the surface of the rat brain occurred. High pressures of about 2.5–2.9 bar were used.

The rats were sacrificed 14 days after traumatization for removal of the brain. After fixation of the brains, sections of thickness 30 mm were prepared in a freezing microtome and stained using Toluidine Blue. For the quantification of the neuronal damage, cell counts were carried out bilaterally in the rostral hippocampus; the proportion of intact cells in the dentate gyrus was determined on the traumatized (right) and the (left) opposite side. The quotient of the cell count in the ipsilateral hippocampus and the number in the contralateral hippocampus was indicated.

REFERENCE EXAMPLE 12
Synthesis of Tested Binding Partners a) 3,4,5,6,7,8-Hexahydro-7-methyl-3-[2-(4-(3-trifluoromethyl-phenyl)piperazin-1-yl)ethyl]pyrido[4',3':4,5]thieno[2,3-d]-pyrimidin-4-one×2HCl (Compound A)

The compound was prepared by heating 2-ethoxymethylenamino-3-cyano-6-methyl-4,5,6,7-tetrahydrothieno-[2,3-c]pyridine or 2-ethoxymethylenamino-3-carboethoxy-6-methyl-4,5,6,7-tetrahydro-thieno[2,3-c]pyridine under reflux with 1-(2-aminoethyl)-4-(3-trifluoromethylphenyl)piperazine in an inert solvent such as ethanol. The reaction mixture was worked up, and the product having a melting point of 309–312° C. was deposited by precipitating with ethereal hydrochloric acid.

A further possibility for the preparation consisted in first heating the abovementioned starting compounds with ethanolamine under reflux in an inert solvent such as ethanol. After the reaction mixture had been worked up, the 3,4,5,6,7,8-hexahydro-3-(2-hydroxy)ethyl-7-methylpyrido[4',3':4,5]thieno[2,3-d]pyrimidin-4-one obtained was reacted, for example, with thionyl chloride in order to introduce a suitable leaving group, so that the reaction of the resulting 3,4,5,6,7,8-hexahydro-3-(2-chloro)-ethyl-7-methylpyrido-[4',3':4,5]thieno[2,3-d]pyrimidin-4-one with N-(3-trifluoromethylphenyl)piperazine in an inert solvent such as xylene under basic conditions (e.g. potassium carbonate) afforded the desired product after working up the reaction mixture.

b) 3,4,5,6,7,8-Hexahydro-6-ethyl-3-[2-(4-(1-naphthyl)piperazin-1-yl)ethyl]pyrido[3',4':4,5]thieno[2,3-d]pyrimidin-4-one×3 HCl×2H$_2$O (Compound B)

Preparation was carried out in principle as described for compound A.

2-Ethoxymethylenamino-3-carboethoxy-5-ethyl-4,5,6,7-tetrahydro-thieno[3,2-c]pyridine was heated under reflux with 1-(2-aminoethyl)-4-(1-naphthyl)piperazine in an inert solvent such as ethanol. The reaction mixture was worked up, and the product converted into the hydrochloride was isolated with a melting point of 298–300° C.

Alternatively, 3-(2-chloroethyl)-6-ethyl-3,4,5,6,7,8-hexahydropyrido[3',4':4,5]thieno[2,3-d]pyrimidin-4-one was reacted under basic conditions with N-(1-naphthyl)piperazine in an inert solvent such as xylene.

c) 3,4,5,6,7,8-Hexahydro-7-methyl-3-[2-(4-(7-methoxynaphth-1-yl) piperazin-1-yl)ethyl]pyrido[4',3':4,5]thieno[2,3-d]pyrimidin-2-one×2 HCl×H$_2$O (Compound C)

Preparation can be carried out analogously to compound A.

Compounds A, B and C and also the intermediates needed for their preparation are known or can be synthesized from analogous starting materials according to the preparation methods described in the literature (F. Sauer and P. Stanetty, Monatsh. Chem. (1975), 106(5), 1111–1116; K. Gewald et al., Chem. Ber. 99, 94–100 (1966), Patent Applications DE 196 36 769.7 and DE 197 24 979.5).

EXAMPLE 1

According to Reference Example 3, the binding affinity of [$^3$H]-5-CT to 5-HT5 receptors was determined. FIG. 1 shows a plot of bound [$^3$H]-5-CT as a function of the [$^3$H]-5-CT concentration. A dissociation constant of $K_d$=0.570 nM was determined. Depending on the clonal cell line, the receptor binding density (B) varied in a range from 900–28,000 fmol/mg of protein.

EXAMPLE 2

According to Reference Example 4, the binding affinities of serotoninergic compounds were determined by means of [$^3$H]-5-CT binding competition. By means of the IC$_{50}$ values obtained, the inhibition constants $K_i$ of the following compounds were determined ($K_i$=IC$_{50}$/(1+C/$K_d$)), where C is the concentration of [$^3$H]-5-CT and $K_d$ was determined according to Example 1):

| Compound | $K_i$ [M] |
| --- | --- |
| R(+)-8-OH-DPAT | 1.25·10$^{-7}$ |
| 5-CT | 1.44·10$^{-9}$ |
| Compound A | 6.61·10$^{-7}$ |
| Compound B | 1.24·10$^{-7}$ |
| Compound C | 2.37·10$^{-7}$ |

EXAMPLE 3

Figure 2:
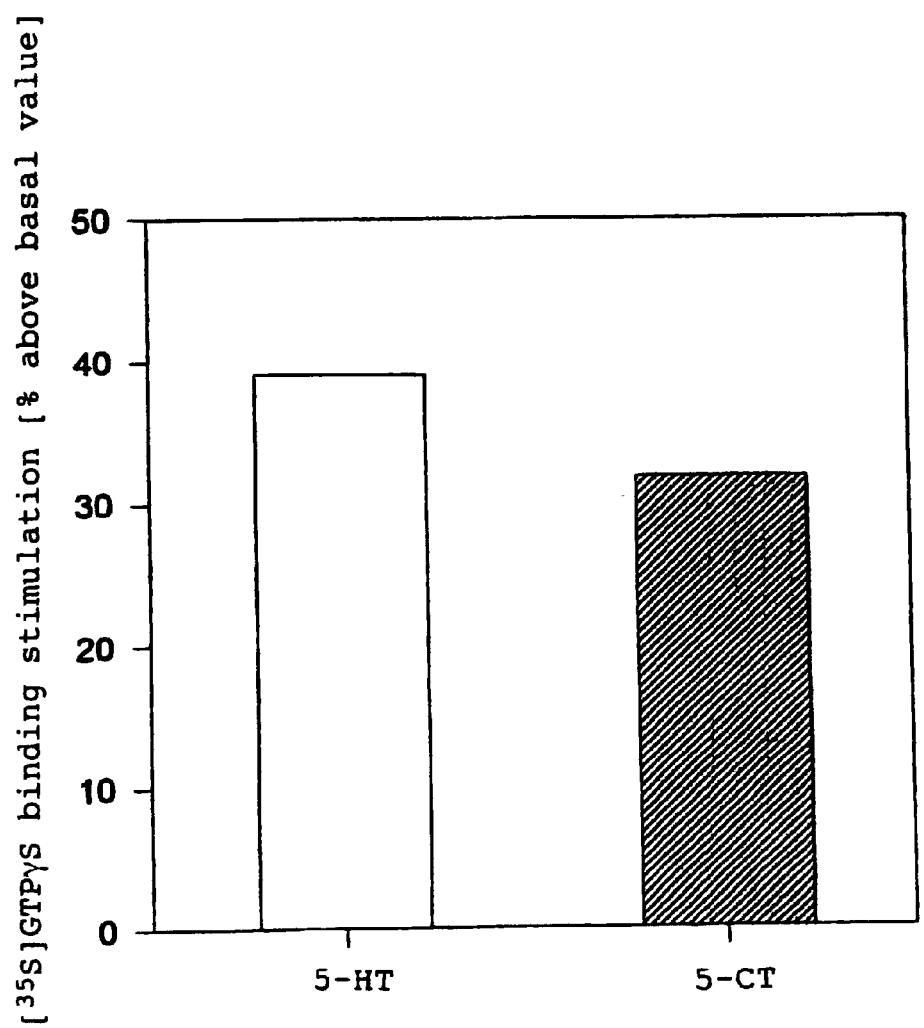
FIG. 2 shows the % above base value of [$^{35}$S] GTPγS binding stimulation.
Figure 3:
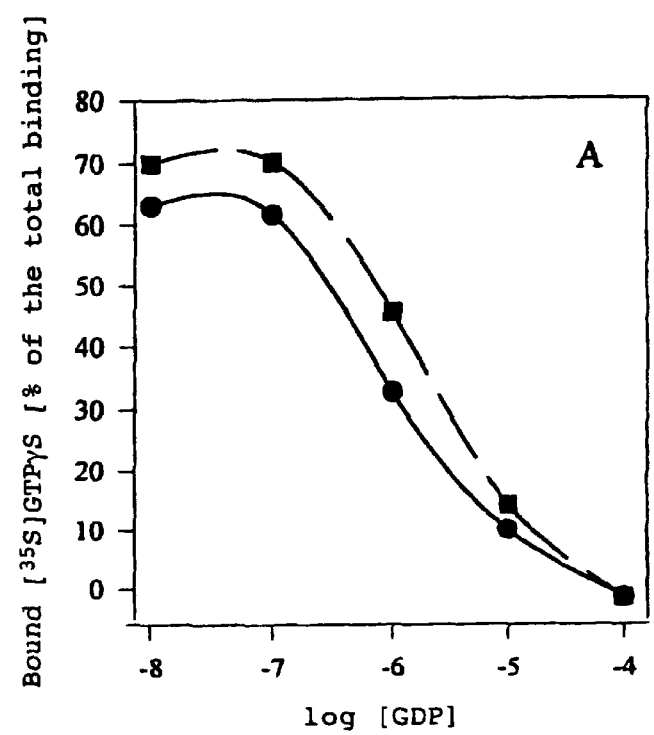
FIG. 3 shows both the % of the total binding of bound [$^{35}$S] GTPγS in relation to the log of the concentration of GDP (Graph A) and of [$^{35}$S] GTPγS binding stimulation in relation to the log of the concentration of GDP (Graph B).
Figure 3:
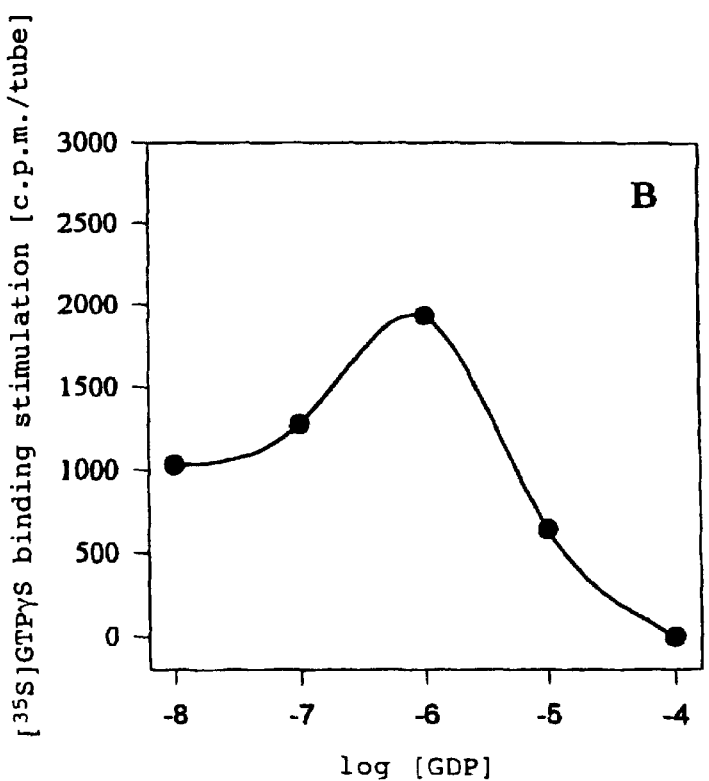
Figure 4:
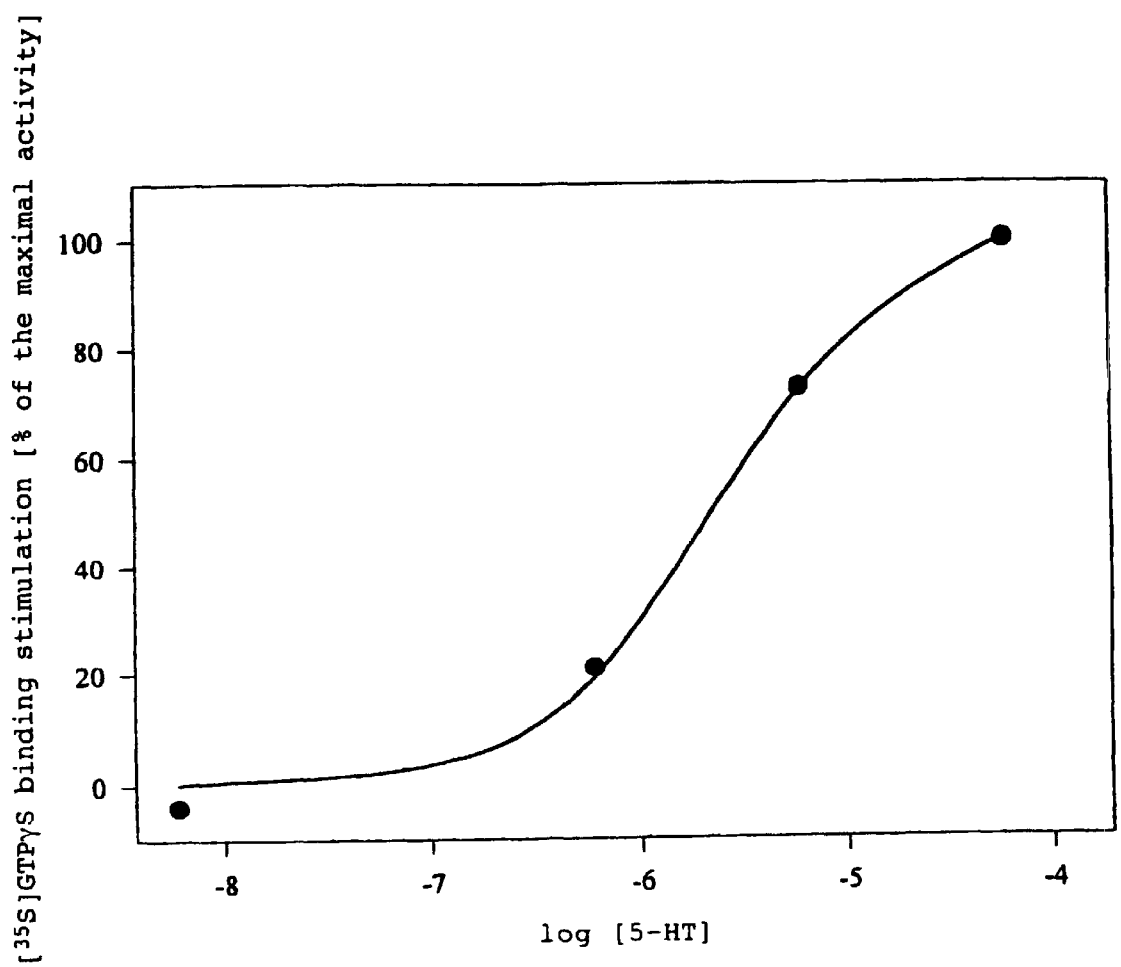
FIG. 4 shows the % of the maximal activity of [$^{35}$S] GTPγS binding stimulation.

According to Reference Example 5, the active compound-induced binding of GTP to G proteins was investigated. The coupling of 5-HT5 receptors to G proteins in HEK293 cells was evident. The typical serotoninergic agonists 5-HT and 5-CT induced an increase in the [$^{35}$S]GTPγS binding to the cell membranes of over 40% above the basic value (see FIG. 2). The 5-HT5 receptor needs GDP for the coupling to G proteins, which is mediated by agonists (see FIG. 3A). The 5-HT effect was dose-dependent (see FIG. 4) with an EC$_{50}$ of 2.6 μM.

EXAMPLE 4

According to Reference Example 10, the neuroprotective action of selected 5-HT5 binding partners was tested. The active compounds were administered intravenously, first as a bolus and then as a maintenance infusion, 90 minutes after MCA occlusion. The following results were achieved:

| Active compound | Dose, i.v. [mg/kg + mg/kg/h] | Infarct volume, % of the control [mean value ± SD, (n)] Placebo | Infarct volume, % of the control [mean value ± SD, (n)] Active compound | P, Student's t test, bilateral |
| --- | --- | --- | --- | --- |
| R(+)-8-OH-DPAT | 2 + 1 | 100 ± 11 (12) | 72 ± 32 (12) | 0.0086 |
| Compound A | 4 + 2 | 100 ± 25 (12) | 62 ± 18 (10) | 0.0013 |
| Compound B | 2 + 1 | 100 ± 20 (12) | 66 ± 19 (9) | 0.0015 |
| Compound C | 1 + 0.5 | 100 | 67 | <0.05 |

EXAMPLE 5

According to Reference Example 11, an experimental brain trauma of the rat was induced using the lateral fluid percussion method. The protective action of the active compounds tested on the survival of hippocampal neurons is expressed as the quotient of the neuron count of the trauma side to the neuron count of the contralateral side; the mean (m) and the mean error of the mean ($s_m$) is in each case indicated

| Active compound | Dose [mg/kg i.p.] | Quotient m ± $s_m$ (n) Placebo | Quotient m ± $s_m$ (n) Active compound | P, Student's t test, bilateral |
| --- | --- | --- | --- | --- |
| Compound C [15 + 120 min post] | 20 + 20 | 0.33 ± 0.05 (10) | 0.56 ± 0.05 (10) | <0.05 |
| Compound B [15 + 120 min post] | 20 + 20 | 0.44 ± 0.03 (17) | 0.64 ± 0.03 (12) | <0.05 |

We claim:

1. An in vitro screening process for the identification of compounds for the treatment of neuropathological disorders and associated signs, symptoms and dysfunctions, which comprises determining the affinity of compounds for 5-HT5 receptors and reading out those 5-HT5 binding partners whose $K_i$ value for binding to 5-HT5 receptors is less than 10$^{-7}$ M and whose binding affinity for 5-HT1A receptors is greater by at most the factor 10 than for 5-HT5 receptors.

2. The process as claimed in claim 1, where compounds are brought into contact with cellular systems having 5-HT5 receptors and their binding affinity is determined.

3. The process as claimed in claim 1, where compounds are brought into contact with cellular systems having 5-HT5 receptors and at least one 5-HT5 binding partner-induced action is determined.

4. The process as claimed in claim 3, where the binding of GTP to G proteins, intracellular calcium levels, the phospholipase C activity and/or the cAMP production are determined.

5. The process as claimed in claim 2, wherein human glioma cell lines or h5-HT5-transfected heterologous cell lines are used.

6. The process as claimed in claim 5, wherein h5-HT5-transfected CHO cells, h5-HT5-transfected human kidney cells, or h5-HT5-transfected C-6 glioma cells are used.

7. A method for treating neurodegenerative disorders and associated signs, symptoms and dysfunctions which comprises administering to a subject in need thereof an effective amount of at least one binding partner for 5-HT5 receptors, the $K_i$ value of the binding partner being less than 10$^{-7}$ M for binding thereof to 5-HT5 receptors and its binding affinity for 5-HT1A receptors being greater by at most the factor 10 than for 5-HT5 receptors.

8. The method as claimed in claim 7, wherein the binding affinity of the binding partner for 5-HT5 receptors is greater than for 5-HT1 A receptors.

9. The method as claimed in claim 7, wherein the neurodegenerative disorder is an ischemic damage.

10. The method as claimed in claim 8, wherein the ischemic damage is a result of brain and spinal cord trauma and also vascular occlusion or heart failure.

11. The method as claimed in claim 7, wherein the neurodegenerative disorder is stroke.

* * * * *